United States Patent
Wright et al.

(10) Patent No.: US 8,092,544 B2
(45) Date of Patent: *Jan. 10, 2012

(54) IMPLANTABLE PATELLA COMPONENT HAVING A THICKENED SUPERIOR EDGE

(75) Inventors: Abraham P. Wright, Winona Lake, IN (US); Wayne M. Goldstein, Highland Park, IL (US)

(73) Assignee: DePuy Products, Inc., Warsaw, IN (US)

( * ) Notice: Subject to any disclaimer, the term of this patent is extended or adjusted under 35 U.S.C. 154(b) by 329 days.

This patent is subject to a terminal disclaimer.

(21) Appl. No.: 12/164,609

(22) Filed: Jun. 30, 2008

(65) Prior Publication Data

US 2009/0326661 A1 Dec. 31, 2009

(51) Int. Cl.
*A61F 2/38* (2006.01)

(52) U.S. Cl. .................. 623/20.18; 623/20.2

(58) Field of Classification Search ............. None
See application file for complete search history.

(56) References Cited

U.S. PATENT DOCUMENTS

| 5,514,183 | A | 5/1996 | Epstein et al. |
| 5,871,540 | A | 2/1999 | Weissman et al. |
| 2003/0033018 | A1 | 2/2003 | Merchant |
| 2003/0181984 | A1 | 9/2003 | Abendschein |

FOREIGN PATENT DOCUMENTS

| EP | 0327297 | 8/1989 |
| EP | 1557144 | 7/2005 |
| EP | 1582184 | 10/2005 |
| GB | 2433698 | 7/2007 |
| WO | 2007102951 | 9/2007 |

OTHER PUBLICATIONS

European Search Report for European Patent Application No. 09164176.1-1526, Dec. 7, 2009, 5 pgs.
Benjamin C. Bengs, MD, and Richard D. Scott, MD; The Effect of Patellar Thickness on Intraoperative Knee Flexion and Patellar Tracking in Total Knee Arthroplasty; Aug. 2006; vol. 21 No. 5; 6pgs.

*Primary Examiner* — David H Willse
*Assistant Examiner* — Javier G Blanco
(74) *Attorney, Agent, or Firm* — Barnes & Thornburg LLP

(57) ABSTRACT

An orthopaedic implant includes a patella component having a posterior bearing surface configured to articulate with the femoral condyles of a femur, and an anterior surface having a number of pegs extending outwardly therefrom. The superior edge of the patella component is thickened relative to conventional dome-shaped patella components.

16 Claims, 6 Drawing Sheets

IMPLANTABLE PATELLA COMPONENT HAVING A THICKENED SUPERIOR EDGE

CROSS REFERENCE

Cross reference is made to copending U.S. patent application Ser. No. _____ entitled "Implantable Patella Component Having a Thickened Superior Edge" by Wayne M. Goldstein and Abraham P. Wright which is assigned to the same assignee as the present application, filed concurrently herewith, and hereby incorporated by reference.

TECHNICAL FIELD

The present disclosure relates generally to an implantable orthopaedic prosthesis, and more particularly to an implantable patella component.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, a orthopaedic prosthesis is implanted into the patient's patella. Specifically, a prosthetic patella component is secured to the patient's natural patella such that its posterior surface articulates with a femoral component during extension and flexion of the knee.

A conventional patella component is embodied as a dome-shaped polymer bearing. Other types of patella components include conforming bearings which attempt to conform with the bearing surfaces of the femur.

SUMMARY

According to one aspect, an orthopaedic implant includes a patella component having a posterior bearing surface configured to articulate with the femoral condyles of a femur and an anterior surface having a number of pegs extending outwardly therefrom.

The superior edge of the patella component is thicker than its inferior edge.

The patella component may also include medial and lateral edges which are of similar size.

The superior edge of the patella component may be thicker than each of its inferior, medial, and lateral edges.

The inferior edge of the patella component may be of similar size to its medial and lateral edges.

The patella component may be embodied as a monolithic polyethylene body.

The curved peak surface of the patella component may be offset in the superior direction from the center of the superior/inferior width of the component.

According to another aspect, an orthopaedic implant includes a patella component having a posterior bearing surface configured to articulate with the femoral condyles of a femur, and an anterior surface having a number of pegs extending outwardly therefrom.

The curved peak surface of the posterior bearing surface may be offset in the superior direction relative to the center of the superior/inferior width of the component.

The superior edge of the patella component may be thicker than its inferior edge.

The inferior edge of the patella component may be of similar size to its medial and lateral edges.

The patella component may be embodied as a monolithic polyethylene body.

The patella component may also include medial and lateral edges which are of similar size.

According to another aspect, an orthopaedic implant includes a patella component having a posterior bearing surface configured to articulate with the femoral condyles of a femur, and an anterior surface having a number of pegs extending outwardly therefrom.

The superior edge of the patella component may be thicker than the medial edge of the component.

The superior edge may also be thicker than the lateral edge of the patella component.

The superior edge may be thicker or of the same thickness as the inferior edge.

The patella component may be embodied as a monolithic polyethylene body.

The patella component may also include medial and lateral edges which are of similar size.

The curved peak surface may be offset in the superior direction relative to the center of the superior/inferior width of the component.

According to another aspect, an orthopaedic implant includes a patella component having a posterior bearing surface configured to articulate with the femoral condyles of a femur, and an anterior surface having a number of pegs extending outwardly therefrom.

The superior edge of the patella component is thicker than both the medial and lateral edges of the component.

The superior edge may be thicker or of the same thickness as the inferior edge.

The patella component may also include medial and lateral edges which are of similar size.

The patella component may be embodied as a monolithic polyethylene body.

The curved peak surface may be offset in the superior direction relative to the center of the superior/inferior width of the component.

According to another aspect, an orthopaedic implant includes a patella component having a posterior bearing surface configured to articulate with the femoral condyles of a femur, and an anterior surface having a number of pegs extending outwardly therefrom.

The posterior bearing surface of the patella component extends away from its curved peak surface in the medial/lateral direction at a steeper angle than it does in the superior/inferior direction.

The superior edge may be thicker or of the same thickness as the inferior edge.

The patella component may also include medial and lateral edges which are of similar size.

The patella component may be embodied as a monolithic polyethylene body.

The curved peak surface may be offset in the superior direction relative to the center of the superior/inferior width of the component.

BRIEF DESCRIPTION OF THE DRAWINGS

The detailed description particularly refers to the following figures, in which.

DETAILED DESCRIPTION OF THE DRAWINGS

Figure 1:
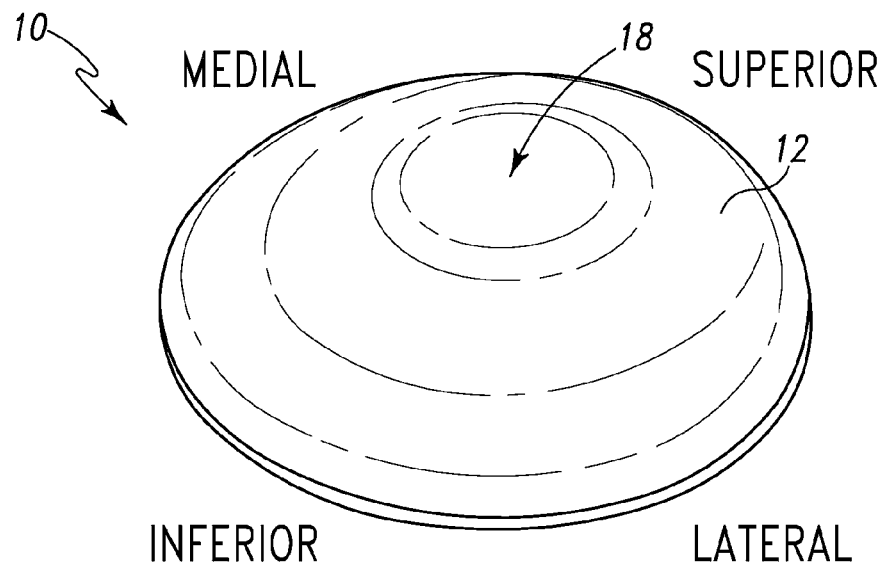
FIG. 1 is a perspective view of a patella component of a knee prosthesis.
Figure 2:
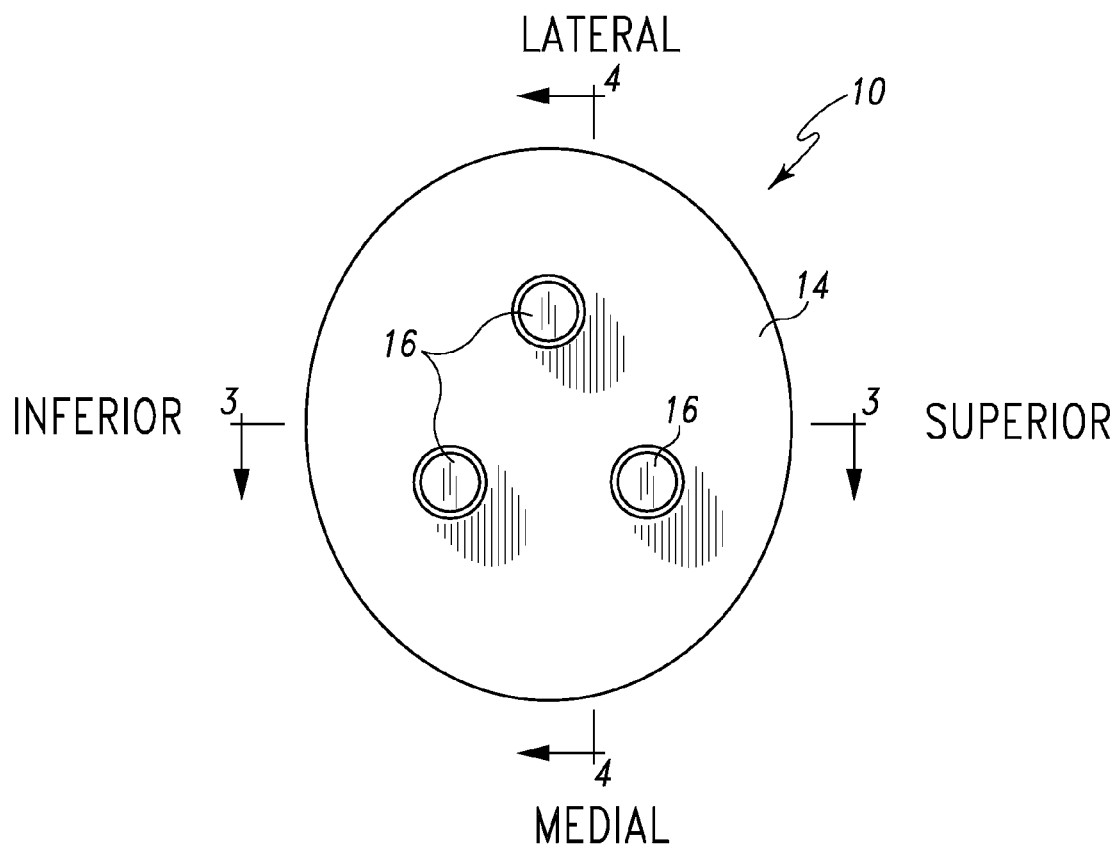
FIG. 2 is a bottom plan view of the patella component of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown a patella component 10 of a knee prosthesis. The patella component 10 includes a posterior bearing surface 12 configured to articulate with the natural or prosthetic condyles of the femur. As used herein, unless noted otherwise, the terms "femur" or "femoral" are intended to mean both natural and prosthetic features of a femur. As such, the term "femoral condyles" is intended to cover both natural femoral condyles and prosthetic femoral condyles. The patella component 10 is embodied as a monolithic polymer body constructed with a material that allows for smooth articulation between the patella component 10 and the femur. One such polymeric material is polyethylene such as ultrahigh molecular weight polyethylene (UHMWPE).

The patella component 10 also includes a flat anterior surface 14 having a number of fixation members, such as pegs 16, extending away therefrom. The pegs 16 are configured to be implanted into a surgically prepared posterior surface of the patient's natural patella (not shown). In such a way, the posterior bearing surface 12 of the patella component 10 faces toward the femur thereby allowing the posterior bearing surface 12 to articulate with the femoral condyles during flexion and extension of the patient's knee.

Figure 3:
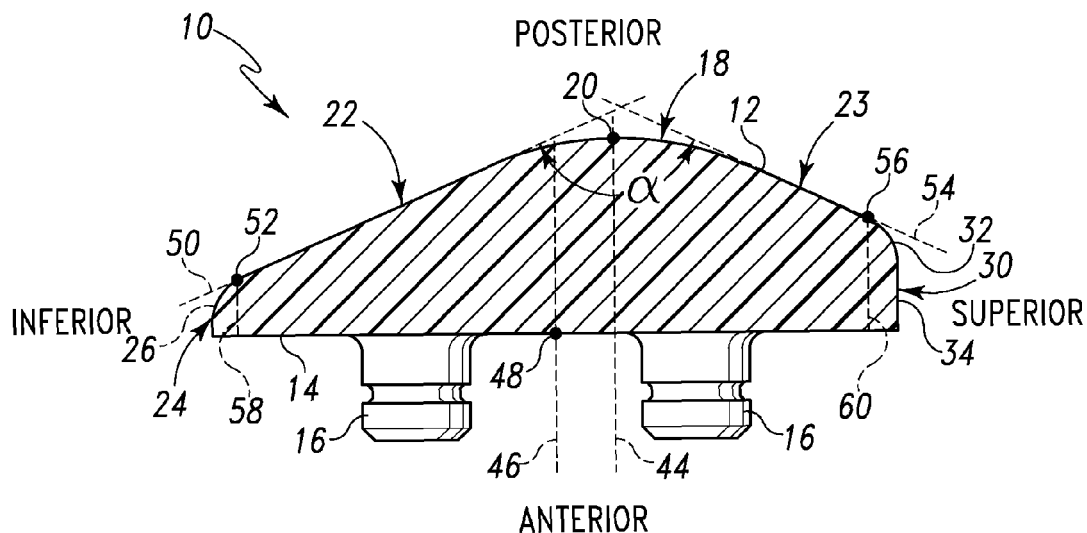
FIG. 3 is a cross sectional view taken in the superior/inferior direction along the line 3-3 of FIG. 1, as viewed in the direction of the arrows.

The posterior bearing surface 12 has a curved peak surface 18. The curved peak surface 18 defines the posterior-most surface of the patella component 10. Specifically, a point on the curved peak surface 18 defines the posterior-most point 20 of the patella component 10. The curved peak surface 18 extends anteriorly from the posterior-most point 20 in the general direction toward the anterior surface 14. In particular, as viewed in FIG. 3, the curved peak surface 18 transitions to a flat inferior surface 22 that extends inferiorly away from the curved peak surface 18. The flat inferior surface 22 in turn transitions to a rounded inferior edge surface 24 that extends inferiorly away from the flat inferior surface 22 in the direction toward the anterior surface 14 of the patella component 10. As shown in FIG. 3, the inferior edge surface 24 is embodied as a curved corner surface 26 that transitions from the flat inferior surface 22 to the anterior surface 14 of the patella component 10.

As also shown in FIG. 3, the curved peak surface 18 transitions to a flat superior surface 28 that extends superiorly away from the curved peak surface 18. The flat superior surface 28 in turn transitions to a rounded superior edge surface 30 that extends superiorly away from the flat superior surface 28 in the direction toward the anterior surface 14 of the patella component 10. The rounded superior edge 30 includes a curved corner surface 32 that transitions from the to the flat superior surface 28 and a flat surface 34 that transitions the curved corner surface 32 to the anterior surface 14 of the patella component 10.

Figure 4:
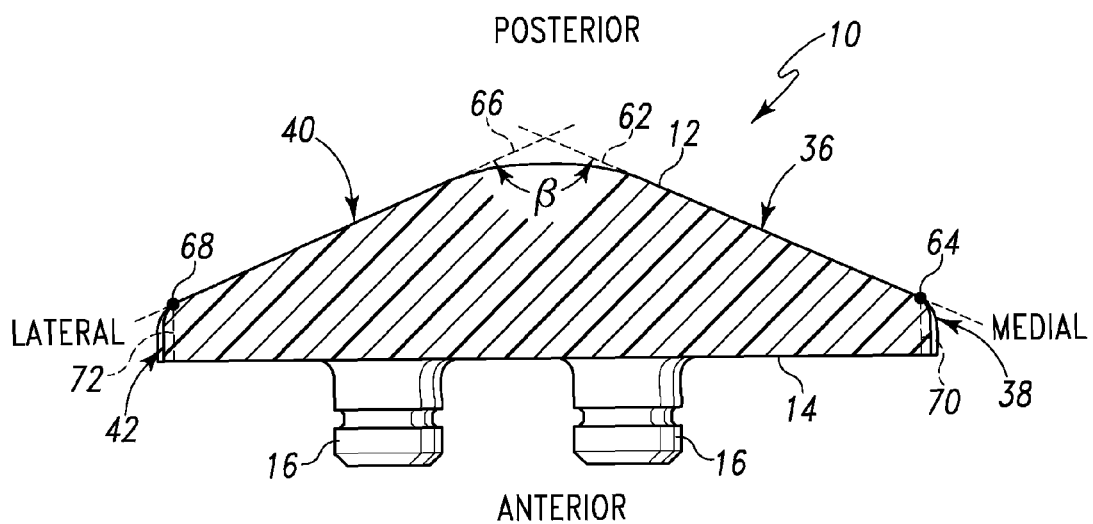
FIG. 4 is a cross sectional view taken in the medial/lateral direction along the line 4-4 of FIG. 1, as viewed in the direction of the arrows.
Figure 5:
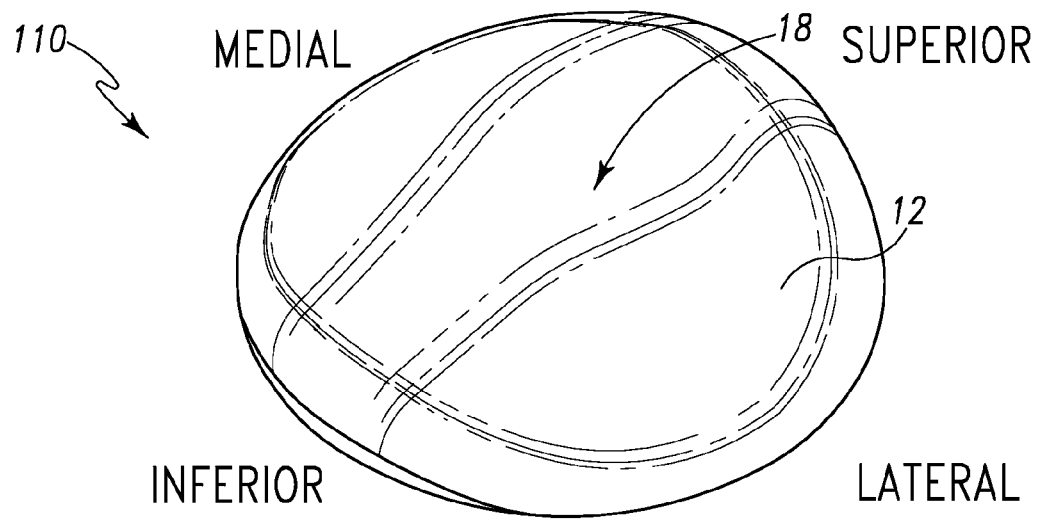
FIG. 5 is a perspective view of another patella component of a knee prosthesis.
Figure 6:
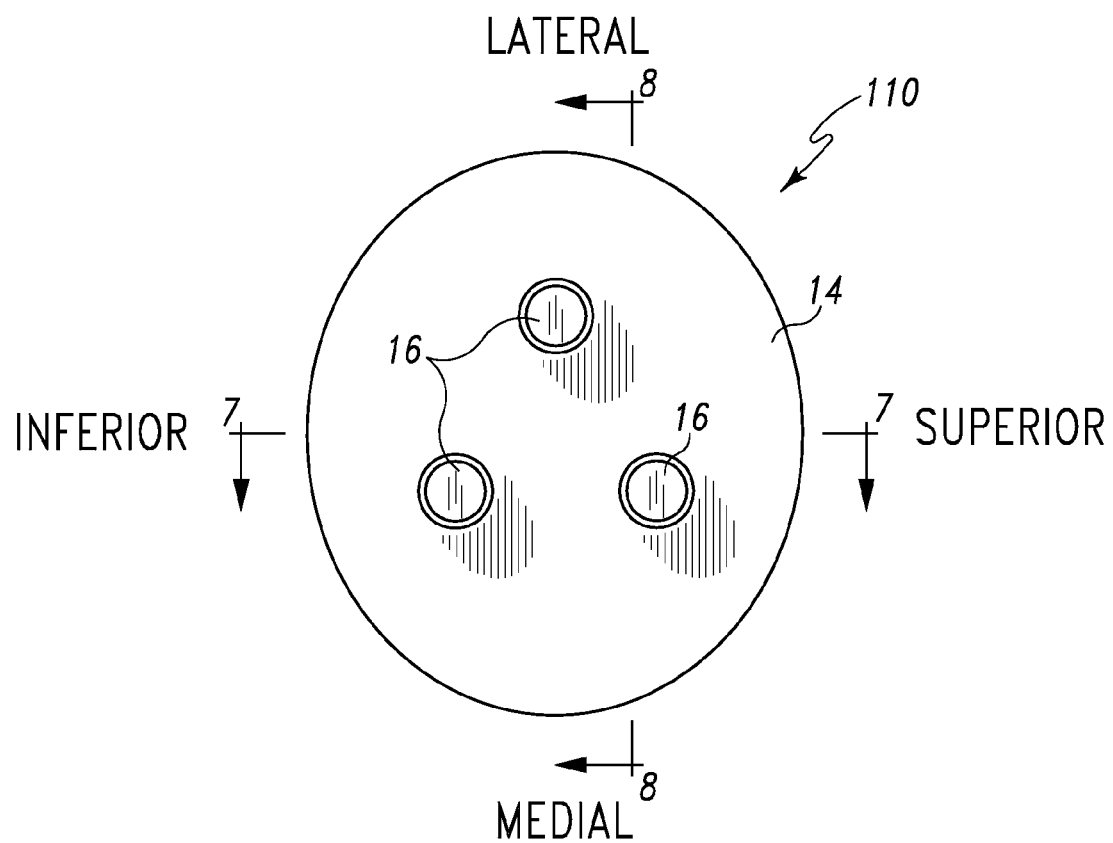
FIG. 6 is a bottom plan view of the patella component of FIG. 5.

As shown in FIG. 4, the curved peak surface 18 transitions to a flat medial surface 36 that extends medially away from the curved peak surface 18. The flat medial surface 36 transitions to a rounded medial edge surface 38 that extends medially away from the flat medial surface 36 in the direction toward the anterior surface 14 of the patella component 10. Similarly, a flat lateral surface 40 extends laterally away from the curved peak surface 18. The flat lateral surface 40 transitions to a rounded lateral edge surface 42 that extends laterally away from the flat lateral surface 40 in the direction toward the anterior surface 14 of the patella component 10.

As shown in FIGS. 1 and 3, the curved peak surface 18 of the patella component 10 is offset in the superior direction relative to conventional dome-shaped patella components in which the tip of curved peak surface (i.e., the posterior-most point) is positioned in the center of the component. Specifically, as can best be seen in FIG. 3, the posterior-most point 20 of the posterior bearing surface 12 is positioned superiorly of the center of the superior/inferior width of the patella component 10. This is demonstrated geometrically in the superior/inferior cross sectional view of FIG. 3 where a pair of imaginary lines extend through the patella component 10 in the anterior/posterior direction. Specifically, an imaginary line 44 extends orthogonally from the anterior surface 14 of the patella component 10 through the posterior-most point 20 of the patella component 10, whereas another imaginary line 46 extends orthogonally from the anterior surface 14 of the patella component 10 through the midpoint 48 of the superior/inferior width of the anterior surface 14 of the patella component 10. As can be seen in FIG. 3, the imaginary line 44 extending through the posterior-most point 20 is parallel to the imaginary line 46 extending through the midpoint 48, but is spaced apart from it in the superior direction.

In the illustrative embodiment of FIGS. 1-4, offsetting the curved peak surface 18 of the patella component 10 in the superior direction in such a manner results in a thickened superior edge relative to conventional dome-shaped patella components in which the tip of the curved peak surface (i.e., the posterior-most point) is positioned in the center of the component. Specifically, as can be seen in FIGS. 3 and 4, the superior edge of the patella component 10 is thicker than its inferior, medial, and lateral edges. Because the edges of the patella component 10 are rounded, such a feature can be demonstrated geometrically in a number of different manners. One way to do so is shown in FIGS. 3 and 4 and described hereinafter. However, it should be appreciated that the relative thickness of each of the component's edges may be demonstrated geometrically in other ways. In the illustrative manner described herein, the tangent point of the edge's rounded corner serves as a common point of reference for determining the thickness of each edge of the patella component 10. Specifically, an imaginary line 50 extends along the flat inferior surface 22 and defines a tangent point 52 at the transition of the flat inferior surface 22 and the rounded inferior edge surface 24. Another imaginary line 54 extends along the flat superior surface 28 and defines a second tangent point 56 at the transition of the flat superior surface 28 and the rounded superior edge surface 30. As can be seen in FIG. 3, an imaginary line segment 58 extends orthogonally from the anterior surface 14 of the patella component 10 to the tangent point 52, whereas another imaginary line segment 60 extends orthogonally from the anterior surface 14 of the patella component 10 to the tangent point 56. Because the superior edge of the patella component 10 is thicker than its inferior edge, the imaginary line segment 60 is longer than the imaginary line segment 58.

As shown in FIG. 4, an imaginary line 62 extends along the flat medial surface 36 and defines a tangent point 64 at the transition of the flat medial surface 36 and the rounded medial edge surface 38. Another imaginary line 66 extends along the flat lateral surface 40 and defines a tangent point 68 at the transition of the flat lateral surface 40 and the rounded lateral edge surface 42. An imaginary line segment 70 extends orthogonally from the anterior surface 14 of the patella component 10 to the tangent point 64, whereas an imaginary line segment 72 extends orthogonally from the anterior surface 14 of the patella component 10 to the tangent point 68. Because the medial and lateral edges are similar in size, the imaginary line segment 70 is equal in length to the imaginary line segment 72.

In the illustrative embodiment of FIGS. 1-4, the superior edge is the thickest edge of the patella component 10. As such, the imaginary line segment 60 is longer than each of the imaginary line segment 58, the imaginary line segment 70, and the imaginary line segment 72. Moreover, because the illustrative embodiment of FIGS. 1-4 is geometrically constructed by offsetting the curved peak surface 18 of the patella component 10 in the superior direction relative to conventional dome-shaped patella components in which the tip of curved peak surface (i.e., the posterior-most point) is positioned in the center of the component, the inferior edge is similar in size to the medial and lateral edges of the component 10. In other words, the imaginary line segment 58 is equal in length each of the imaginary line segment 70 and the imaginary line segment 72. It should be appreciated, however, that such need not be the case. For example, it is contemplated that the inferior edge could be thinner than the medial and lateral edges. Moreover, as will be discussed below in greater detail, the inferior edge could be thicker than the medial and lateral edges.

In the illustrative embodiment of FIGS. 1-4, the posterior bearing surface 12 extends away from the posterior-most point 20 of the curved peak surface 18 at a similar angle in all directions. This is shown geometrically in FIGS. 3 and 4 in the angles created by the intersection of the imaginary lines extending along the flat surfaces of the posterior bearing surface 12. Specifically, the imaginary line 50 that extends along the flat inferior surface 22 intersects the imaginary line 54 that extends along the flat superior surface 28 to define an angle of intersection ($\alpha$), whereas, the imaginary line 62 that extends along the flat medial surface 36 intersects the imaginary line 66 that extends along the flat lateral surface 40 to define an angle of intersection ($\beta$). In the exemplary embodiment of FIGS. 1-4, the angle of intersection ($\alpha$) is equal to the angle of intersection ($\beta$). In other words, the posterior bearing surface 12 extends away from the posterior-most point 20 of the curved peak surface 18 at the same angle in the superior/inferior direction as it does in the medial/lateral direction. In the specific illustrative embodiment of FIGS. 1-4, the angles of intersection ($\alpha$, $\beta$) are both approximately 130°. In such an arrangement (i.e., one in which the posterior bearing surface 12 extends away from the curved peak surface 18 at a common angle in each direction), the thickened superior edge of the patella component 10 is created, conceptually, by the "shortening" of the superior side of the component as a result of having an offset peak.

Another embodiment of a patella component 110 is shown in FIGS. 5-8. The patella component 110 shares many similarities with the patella component 10. As such, like reference numerals are utilized in FIGS. 1-8 to refer to like structures and features.

Like the patella component 10 of FIGS. 1-4, the patella component 110 of FIGS. 5-8 has a curved peak surface 18 that is offset in the superior direction relative to conventional dome-shaped patella components in which the tip of curved peak surface (i.e., the posterior-most point) is positioned in the center of the component. As a result, as can best be seen in FIG. 7, the posterior-most point 20 of the posterior bearing surface 12 is positioned superiorly of the center of the superior/inferior width of the patella component 110. This is demonstrated geometrically in the superior/inferior cross sectional view of FIG. 7 where the imaginary line 44 extending through the posterior-most point 20 is parallel to the imaginary line 46 extending through the midpoint 48, but is spaced apart from it in the superior direction. In the illustrative embodiment shown in FIGS. 5-8, the patella component 110 has a greater superior offset relative to the patella component 10. In other words, the distance between the imaginary line 44 and the imaginary line 46 is greater in FIGS. 5-8 relative to the embodiment shown in FIGS. 1-4. In the illustrative embodiments described herein, the magnitude of the superior offset is 3-5 mm. It should be appreciated, however, the magnitude of the superior offset may be altered in the either embodiment to fit the needs of a given design of a patella component.

Figure 7:
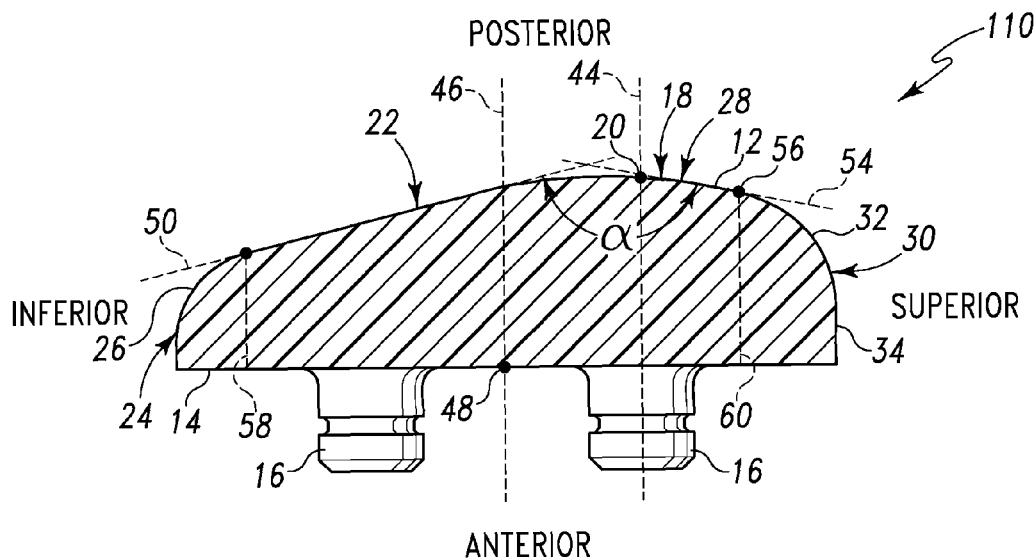
FIG. 7 is a cross sectional view taken in the superior/inferior direction along the line 7-7 of FIG. 5, as viewed in the direction of the arrows.
Figure 8:
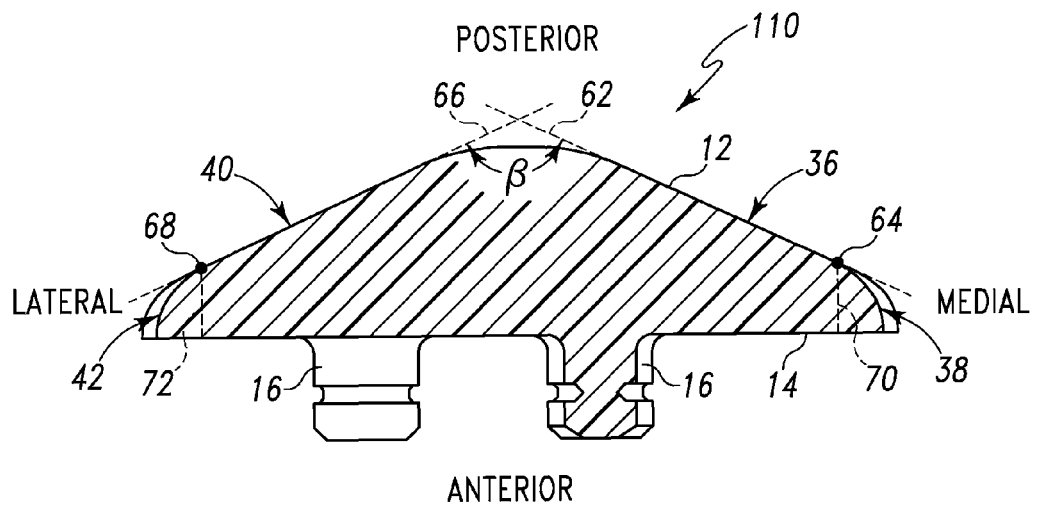
FIG. 8 is a cross sectional view taken in the medial/lateral direction along the line 8-8 of FIG. 5, as viewed in the direction of the arrows.
Figure 9:
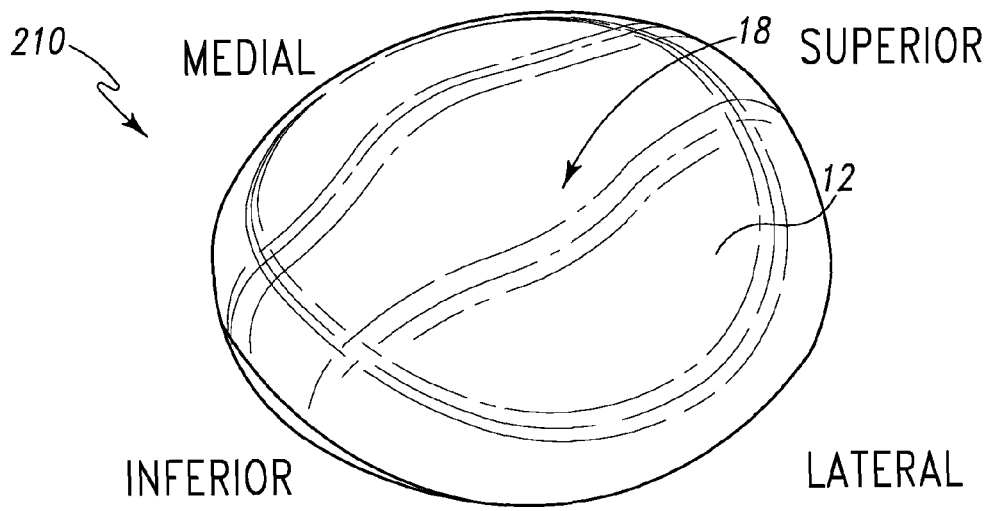
FIG. 9 is a perspective view of yet another patella component of a knee prosthesis.
Figure 10:
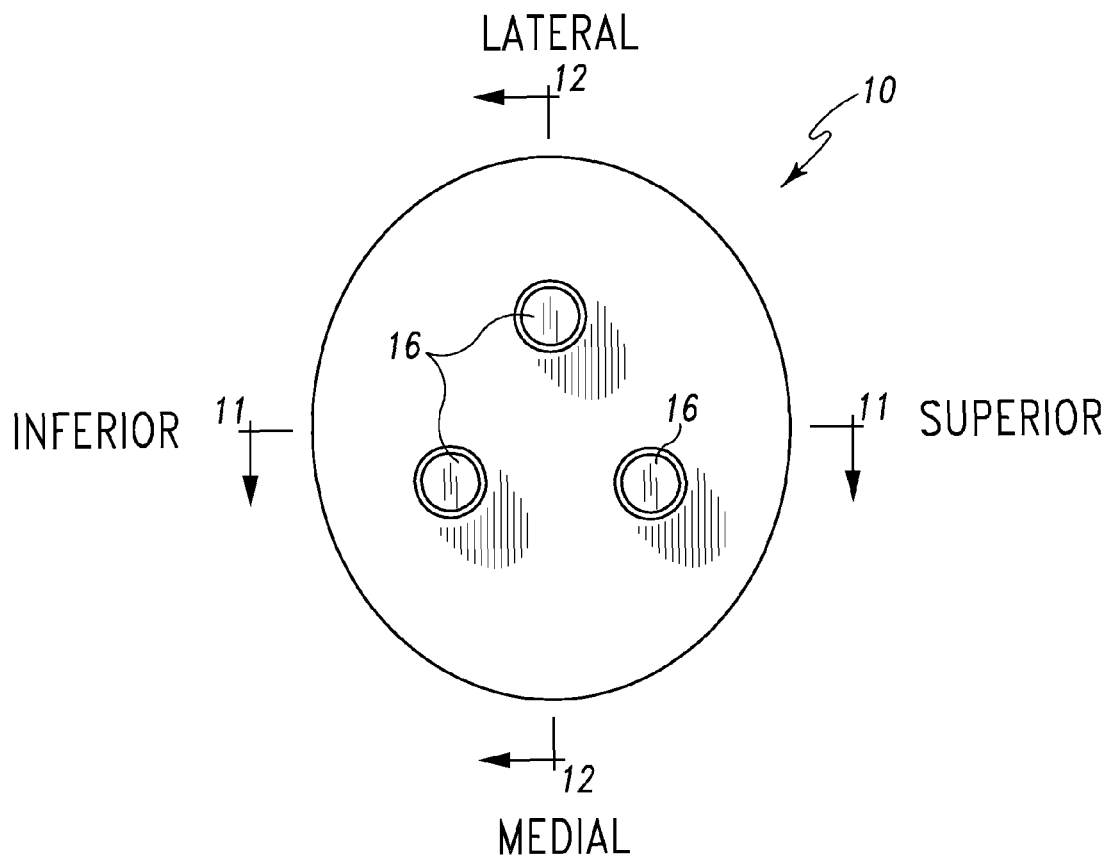
FIG. 10 is a bottom plan view of the patella component of FIG. 9.

Like the patella component 10, the superior edge of the patella component 110 is thickened relative to conventional dome-shaped patella components in which the tip of the curved peak surface (i.e., the posterior-most point) is positioned in the center of the component. Specifically, as can be seen in FIGS. 7 and 8, the superior edge of the patella component 110 is thicker than its inferior, medial, and lateral edges. Such a feature can be demonstrated geometrically in a similar manner to as described above in regard to FIGS. 1-4, that is, by using the tangent point of the edge's rounded corner as a common point of reference for determining the thickness of each edge of the patella component 110. As described above in detail, and not repeated here for purposes of brevity, the length of imaginary line segments extending orthogonally from the anterior surface 14 of the patella component 110 through the respective tangent point of each edge may be used to demonstrate the differences in thickness of the component's edges. Specifically, because the superior edge of the patella component 110 is thicker than its inferior edge, the imaginary line segment 60 is longer than the imaginary line segment 58.

Like the patella component 10, the medial and lateral edges of the patella component 110 are of similar size. As such, the imaginary line segment 70 extending orthogonally from the anterior surface 14 through the tangent point 64 is equal in length to the imaginary line segment 72 extending orthogonally from the anterior surface 14 through the tangent point 68. However, unlike the patella component 10 in which its inferior edge is similar, or even smaller in size, relative to its medial and lateral edges, the inferior edge of the component 110 is thicker than its medial and lateral edges. As a result, the imaginary line segment 58 extending orthogonally from the anterior surface 14 through the tangent point 52 is longer than each of the imaginary line segment 70 and the imaginary line segment 72.

Unlike the patella component 10 in which the posterior bearing surface 12 extends away from the curved peak surface 18 at a common angle in each direction, the posterior bearing surface 12 of the patella component 110 extends away from the curved peak surface 18 in the medial/lateral direction at a steeper angle than it does in the superior/inferior direction. This is shown geometrically in FIGS. 7 and 8 where the angle of intersection (α) formed by the intersection of the imaginary line 50 extending along the flat inferior surface 22 and the imaginary line 54 extending along the flat superior surface 28 is greater than the angle of intersection (β) formed by the intersection of the imaginary line 62 extending along the flat medial surface 36 and the imaginary line 66 extending along the flat lateral surface 40. In the specific illustrative embodiment of FIGS. 5-8, the angle of intersection (α) is approximately 152°, whereas the angle of intersection (β) is approximately 130°.

Referring now to FIGS. 9-12, yet another embodiment of a patella component 210 is shown. The patella component 210 shares many similarities with the patella components 10, 110. As such, like reference numerals are utilized in FIGS. 1-12 to refer to like structures and features.

Unlike the patella components 10, 110, the curved peak surface 18 of the patella component 210 is not offset in the superior direction, but rather is similar in design to a conventional dome-shaped patella components in which the tip of curved peak surface (i.e., the posterior-most point) is positioned in the center of the component. As a result, and as can best be seen in FIG. 11, the posterior-most point 20 of the posterior bearing surface 12 is aligned with the center of the superior/inferior width of the patella component 210. This is demonstrated geometrically in the superior/inferior cross sectional view of FIG. 11 where the imaginary line 44 extending through the posterior-most point 20 is coincident with the imaginary line 46 extending through the midpoint 48. In other words, the imaginary line 44 and the imaginary line 46 form a common line.

Like the patella components 10, 110, the medial and lateral edges of the patella component 210 are of similar size. Such a feature can be demonstrated geometrically in a similar manner to as described above in regard to FIGS. 1-4, that is, by using the tangent point of the edge's rounded corner as a common point of reference for determining the thickness of each edge of the patella component 210. As described above in detail, and not repeated here for purposes of brevity, the length of the imaginary line segment 70 extending orthogonally from the anterior surface 14 through the tangent point 64 is equal to the length of the imaginary line segment 72 extending orthogonally from the anterior surface 14 through the tangent point 68.

Figure 11:
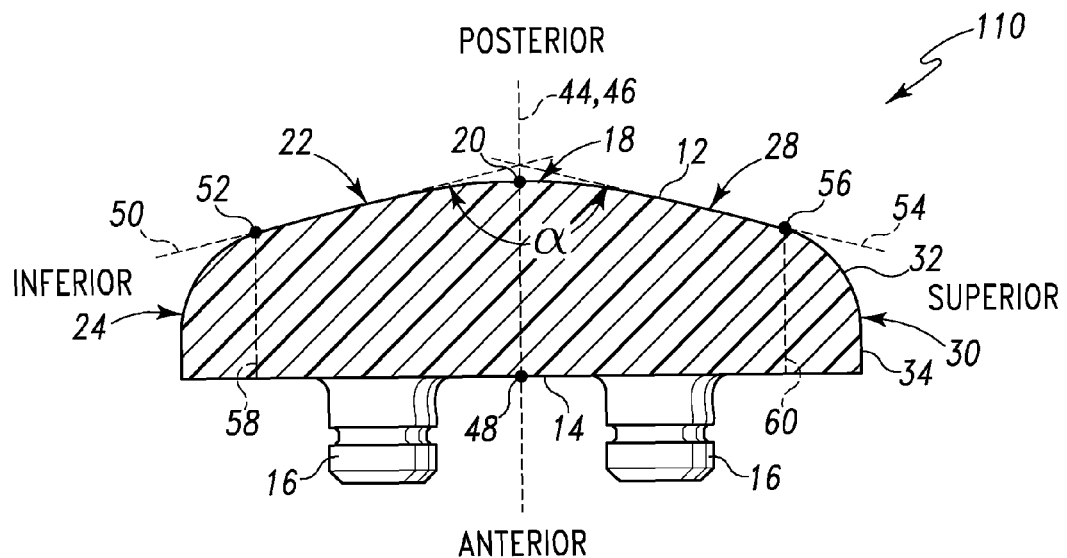
FIG. 11 is a cross sectional view taken in the superior/inferior direction along the line 11-11 of FIG. 9, as viewed in the direction of the arrows.
Figure 12:
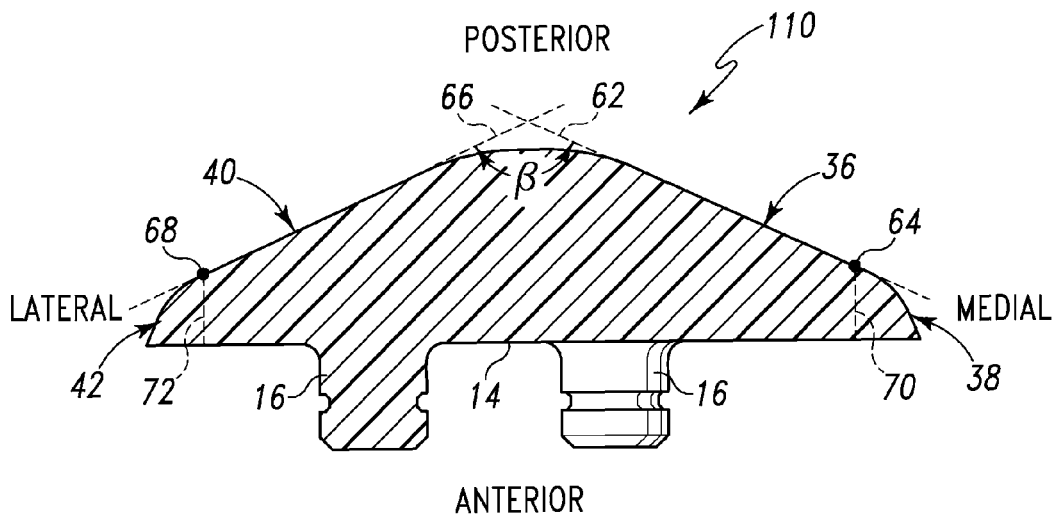
FIG. 12 is a cross sectional view taken in the medial/lateral direction along the line 12-12 of FIG. 9, as viewed in the direction of the arrows.

Also like the patella components 10, 110, the superior edge of the patella component 210 is thicker than the component's medial and lateral edges. Specifically, as can be seen in FIGS. 11 and 12, the superior edge of the patella component 210 is thicker than its medial and lateral edges. Because the superior edge of the patella component 210 is thicker than its medial and lateral edges, the imaginary line segment 60 of the patella component 210 is longer than each of the imaginary line segment 70 and the imaginary line segment 72.

However, unlike the patella components 10, 110 which have superior edges that are thicker than their inferior edges, the inferior edge of the component 210 is similar in size to its superior edge. As a result, the length of the imaginary line segment 58 extending orthogonally from the anterior surface 14 of the component 210 through the tangent point 52 is equal to the length of the imaginary line segment 60 extending orthogonally from the anterior surface 14 of the component 210 through the tangent point 56. In such an arrangement, both the superior edge and the inferior edge of the patella component 210 are thicker than either of its medial and lateral edges. In other words, both the imaginary line segment 58 extending orthogonally from the anterior surface 14 of the component 210 through the tangent point 52 and the imaginary line segment 60 extending orthogonally from the anterior surface 14 of the component 210 through the tangent point 56 are longer than both the imaginary line segment 70 extending orthogonally from the anterior surface 14 through the tangent point 64 and the imaginary line segment 72 extending orthogonally from the anterior surface 14 through the tangent point 68.

Like the patella component 110, the posterior bearing surface 12 of the patella component 210 extends away from the curved peak surface 18 in the medial/lateral direction at a steeper angle than it does in the superior/inferior direction. Specifically, as shown geometrically in FIGS. 11 and 12, the angle of intersection (α) formed by the intersection of the imaginary line 50 extending along the flat inferior surface 22 and the imaginary line 54 extending along the flat superior surface 28 is greater than the angle of intersection (β) formed by the intersection of the imaginary line 62 extending along the flat medial surface 36 and the imaginary line 66 extending along the flat lateral surface 40. In the specific illustrative embodiment of FIGS. 9-12, the angle of intersection (α) is approximately 152°, whereas the angle of intersection (β) is approximately 130°.

Numerous embodiments of patella components have been described herein. Each of such embodiments includes a superior edge which has been thickened relative to the design of conventional dome-shaped patella components in which the superior edge shares a common size with the component's remaining edges. Certain of the embodiments of the patella components described herein also include inferior edges that are thicker than the medial and lateral edges of the component. Certain of the embodiments of the patella components described herein also include a posterior bearing surface in which the curved peak surface thereof is offset in the superior direction relative to conventional dome-shaped patella components. It should be appreciated that the dimensional magnitude of such features may be varied to fit the needs of a given design of a patella component. In particular, a given design of a patella component is typically made commercially available in a variety of different sizes, particularly in a variety of different lengths and widths. This is done to accommodate the many variations in patient size and anatomy across a population. As such, the dimensions of a given design of the patella components 10, 110, 210, including the thickness of a given edge or the magnitude of the offset of the curved peak surface, may also be varied to accommodate such variations in patient size and anatomy across a population.

Moreover, it should also be appreciated that the features of the various embodiments described herein may also be combined as needed to fit the design of a given patella component. For example, patella components having medial and lateral edges with differing thicknesses may be utilized. As a further example, a patella component having a centered curved peak surface (e.g., in a similar manner to the patella component 210) may be embodied with a superior edge that is thicker than its inferior edge (e.g., in a similar manner to the patella components 10, 110).

Each of the patella components described herein includes a superior edge which has been thickened relative to the design of conventional dome-shaped patella components in which the superior edge shares a common size with the component's remaining edges. Unexpectedly, such a design helps resist the tendency of the patella component to extend during deep flexion of the knee. Moreover, such a design has also unexpectedly contributed to a reduction in polymer deformation on the superior edge of the patella component.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An orthopaedic implant, comprising:
a patella component having (i) a posterior bearing surface configured to articulate with the femoral condyles of a femur, and (ii) an anterior surface having a number of pegs extending outwardly therefrom,
wherein, when viewed in a cross sectional view taken in the superior/inferior direction, the posterior bearing surface has (i) a curved peak surface that defines the posterior-most surface of the patella component, (ii) a flat superior surface that extends superiorly away from the curved peak surface, (iii) a rounded superior edge surface that extends superiorly away from the flat superior surface in the direction toward the anterior surface of the patella component, (iv) a flat inferior surface that extends inferiorly away from the curved peak surface, and (v) a rounded inferior edge surface that extends inferiorly away from the flat inferior surface in the direction toward the anterior surface of the patella component,
wherein, when viewed in a cross sectional view taken in the medial/lateral direction, the posterior bearing surface has (i) a flat medial surface that extends medially away from the curved peak surface, and (ii) a rounded medial edge surface that extends inferiorly away from the flat medial surface in the direction toward the anterior surface of the patella component,
wherein (i) a first imaginary line extends along the flat superior surface and defines a first tangent point at the transition of the flat superior surface and the rounded superior edge surface, (ii) a second imaginary line extends along the flat inferior surface and defines a second tangent point at the transition of the flat inferior surface and the rounded inferior edge surface, (iii) a third imaginary line extends along the flat medial surface and defines a third tangent point at the transition of the flat medial surface and the rounded medial edge surface, (iv) a first imaginary line segment extends orthogonally from the anterior surface of the patella component to the first tangent point, (v) a second imaginary line segment extends orthogonally from the anterior surface of the patella component to the second tangent point, (vi) a third imaginary line segment extends orthogonally from the anterior surface of the patella component to the third tangent point, (vii) the first imaginary line segment is longer than the second imaginary line segment, (viii) the second imaginary line segment is longer than the third imaginary line segment, (ix) a point on the curved peak surface defines the posterior-most point of the patella component, (x) a fourth imaginary line extends orthogonally from the anterior surface of the patella component through the posterior-most point of the patella component, (xi) a fifth imaginary line extends orthogonally from the anterior surface of the patella component through the midpoint of the superior/inferior width of the anterior surface of the patella component, and (xii) the fourth imaginary line is parallel to, and spaced apart from, the fifth imaginary line.

2. The orthopaedic implant of claim 1, wherein:
when viewed in the cross sectional view taken in the medial/lateral direction, the posterior bearing surface has (i) a flat lateral surface that extends laterally away from the curved peak surface, and (ii) a rounded lateral edge surface that extends laterally away from the flat lateral surface in the direction toward the anterior surface of the patella component, and
a sixth imaginary line extends along the flat lateral surface and defines a fourth tangent point at the transition of the flat lateral surface and the rounded lateral edge surface,
a sixth imaginary line segment extends orthogonally from the anterior surface of the patella component to the fourth tangent point, and
the second imaginary line segment is longer than the sixth imaginary line segment.

3. The orthopaedic implant of claim 2, wherein the third imaginary line segment is equal in length to the sixth imaginary line segment.

4. The orthopaedic implant of claim 1, wherein the rounded superior edge surface comprises (i) a curved corner surface connected to the flat superior surface, and (ii) a flat surface that connects the curved corner surface to the anterior surface of the patella component.

5. The orthopaedic implant of claim 1, wherein the patella component comprises a monolithic polyethylene body.

6. The orthopaedic implant of claim 1, wherein:
the curved peak surface transitions superiorly to the flat superior surface, inferiorly to the flat inferior surface, and medially to the flat medial surface,
the flat superior surface transitions to the rounded superior edge surface,
the flat inferior surface transitions to the rounded inferior edge surface, and the flat medial surface transitions to the rounded medial edge surface.

7. The orthopaedic implant of claim 6, wherein:
the rounded superior edge surface transitions to the anterior surface of the patella component,
the rounded inferior edge surface transitions to the anterior surface of the patella component, and
the rounded medial edge surface transitions to the anterior surface of the patella component.

8. An orthopaedic implant, comprising:
a patella component having (i) a posterior bearing surface configured to articulate with the femoral condyles of a femur, and (ii) an anterior surface having a number of pegs extending outwardly therefrom,
wherein, when viewed in a cross sectional view taken in the superior/inferior direction, the posterior bearing surface has (i) a curved peak surface that defines the posterior-most surface of the patella component, (ii) a flat superior surface that extends superiorly away from the curved peak surface, (iii) a flat inferior surface that extends inferiorly away from the curved peak surface, (iv) a rounded superior edge surface that extends superiorly away from the flat superior surface in the direction toward the anterior surface of the patella component, and (v) a rounded inferior edge surface that extends inferiorly away from the flat inferior surface in the direction toward the anterior surface of the patella component,
wherein, when viewed in a cross sectional view taken in the medial/lateral direction, the posterior bearing surface has (i) a flat medial surface that extends medially away from the curved peak surface (ii) a flat lateral surface that extends laterally away from the curved peak surface, (iii) a rounded medial edge surface that extends medially away from the flat medial surface in the direction toward the anterior surface of the patella component, and (iv) a rounded lateral edge surface that extends laterally away from the flat lateral surface in the direction toward the anterior surface of the patella component,
wherein (i) a first imaginary line extends along the flat superior surface and defines a first tangent point at the transition of the flat superior surface and the rounded superior edge surface, (ii) a second imaginary line extends along the flat inferior surface defines a second tangent point at the transition of the flat inferior surface and the rounded inferior edge surface, and intersects the first imaginary line to define a first angle of intersection therebetween, (iii) a third imaginary line extends along the flat medial surface and defines a third tangent point at the transition of the flat medial surface and the rounded medial edge surface, (iv) a fourth imaginary line extends along the flat lateral surface, defines a fourth tangent point at the transition of the flat lateral surface and the rounded lateral edge surface, and intersects the third imaginary line to define a second angle of intersection therebetween, (v) the first angle of intersection is greater than the second angle of intersection, (vi) a first imaginary line segment extends orthogonally from the anterior surface of the patella component to the first tangent point, (vii) a second imaginary line segment extends orthogonally from the anterior surface of the patella component to the second tangent point, (viii) a third imaginary line segment extends orthogonally from the anterior surface of the patella component to the third tangent point, (ix) a fourth imaginary line segment extends orthogonally from the anterior surface of the patella component to the fourth tangent point, (x) the length of the first imaginary line segment is greater than or equal to the length of the second imaginary line segment, (xi) and the first imaginary line segment is longer than both the third imaginary line segment and the fourth imaginary line segment.

9. The orthopaedic implant of claim 8,
wherein the first imaginary line segment is equal in length to the second imaginary line segment.

10. The orthopaedic implant of claim 8, wherein the first imaginary line segment is longer than the second imaginary line segment.

11. The orthopaedic implant of claim 8, wherein the third imaginary line segment is equal in length to the fourth imaginary line segment.

12. The orthopaedic implant of claim 8, wherein the rounded superior edge surface comprises (i) a curved corner surface connected to the flat superior surface, and (ii) a flat surface that connects the curved corner surface to the anterior surface of the patella component.

13. The orthopaedic implant of claim 8, wherein:
the curved peak surface transitions (i) superiorly to the flat superior surface, (ii) inferiorly to the flat inferior surface, (iii) medially to the flat medial surface, and (iv) laterally to the flat lateral surface,
the flat superior surface transitions to the rounded superior edge surface,
the flat inferior surface transitions to the rounded inferior edge surface,
the flat medial surface transitions to the rounded medial edge surface, and
the flat lateral surface transitions to the rounded lateral edge surface.

14. The orthopaedic implant of claim 13, wherein:
the rounded superior edge surface transitions to the anterior surface of the patella component,
the rounded inferior edge surface transitions to the anterior surface of the patella component, and
the rounded medial edge surface transitions to the anterior surface of the patella component, and
the rounded lateral edge surface transitions to the anterior surface of the patella component.

15. The orthopaedic implant of claim 8, wherein the patella component comprises a monolithic polyethylene body.

16. The orthopaedic implant of claim 8, wherein:
a point on the curved peak surface defines the posterior-most point of the patella component,
a fifth imaginary line extends orthogonally from the anterior surface of the patella component through the posterior-most point of the patella component,
a sixth imaginary line extends orthogonally from the anterior surface of the patella component through the midpoint of the superior/inferior width of the anterior surface of the patella component, and
the fifth imaginary line is parallel to, and spaced apart from, the sixth imaginary line.

* * * * *